United States Patent [19]
Danielsson et al.

[11] Patent Number: 5,792,063
[45] Date of Patent: Aug. 11, 1998

[54] DEVICE FOR MONITORING MEASUREMENT ELECTRODES, DEVISED FOR PICKING UP PHYSIOLOGICAL MEASUREMENT SIGNALS, AND THEIR LEADS

[75] Inventors: Peter Danielsson, Solna; Thomas Ohlsson, Hässelby, both of Sweden

[73] Assignee: Siemens Elema AB, Solna, Sweden

[21] Appl. No.: 834,664

[22] Filed: Apr. 11, 1997

[30] Foreign Application Priority Data

Apr. 12, 1996 [SE] Sweden .................................. 9601387

[51] Int. Cl.$^6$ ............................................. A61B 5/04
[52] U.S. Cl. ............................................. 600/509
[58] Field of Search ................................... 600/508, 509

[56] References Cited

U.S. PATENT DOCUMENTS 3,602,215  8/1971  Parnell .................................. 600/508
4,993,423  2/1991  Stige ..................................... 600/509
5,020,541  6/1991  Mariott ................................. 600/509

Primary Examiner—William E. Kamm
Attorney, Agent, or Firm—Hill & Simpson

[57] ABSTRACT

In a device for monitoring measurement electrodes, attached to a patient in order to pick up physiological measurement signals, and a neutral electrode and associated leads at the same time as physiological measurement signals are picked up, each measurement electrode is connected to an input terminal on its associated measurement amplifier. A test signal generator is arranged to generate a pure AC signal, without any direct current component, across the neutral electrode attached to a patient during the pickup of measurement signals.

13 Claims, 6 Drawing Sheets

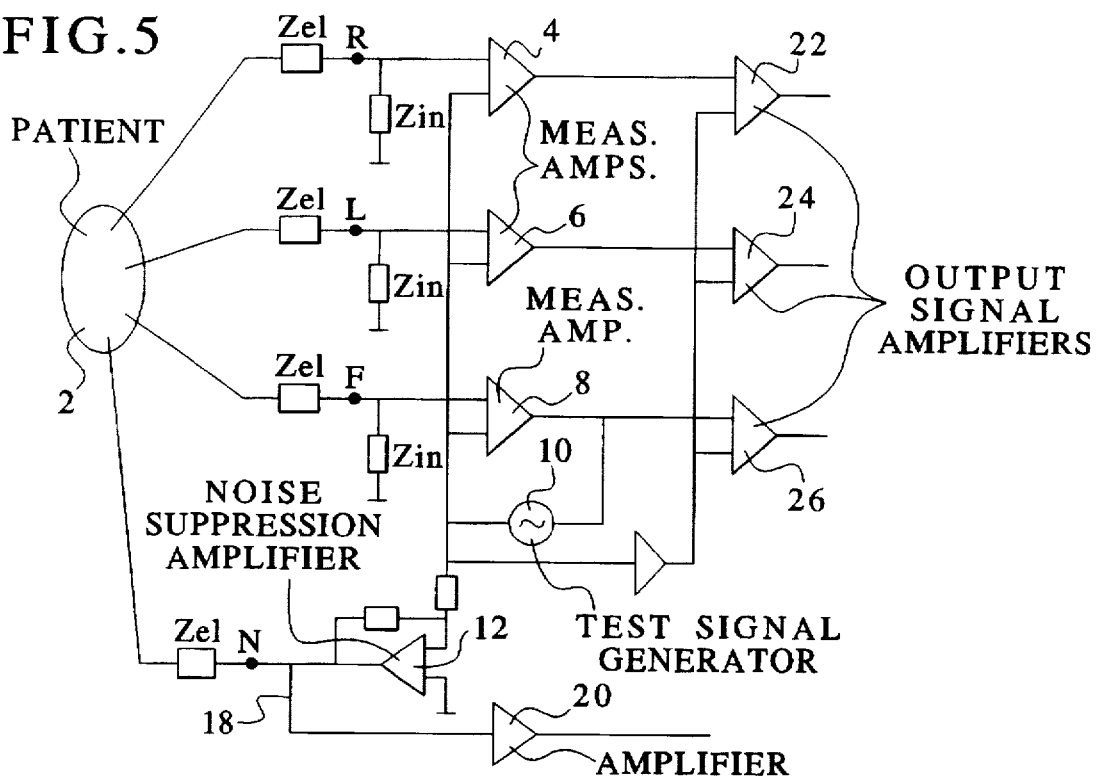
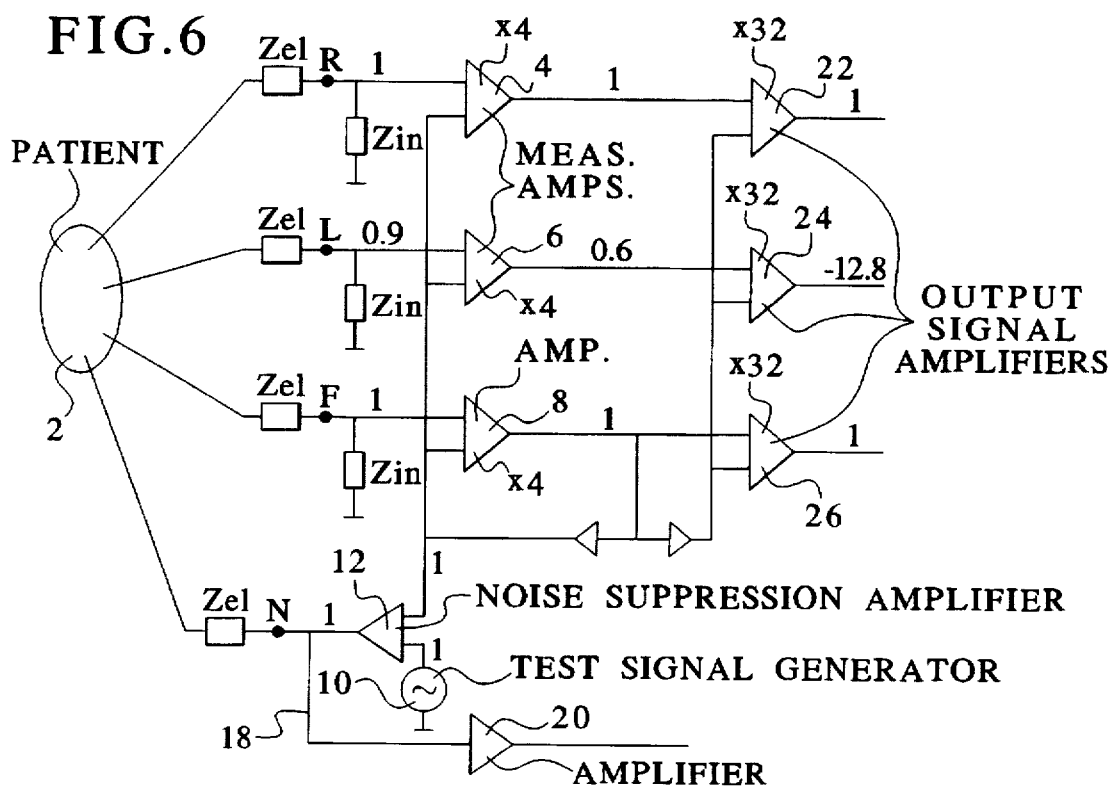

5,792,063

DEVICE FOR MONITORING MEASUREMENT ELECTRODES, DEVISED FOR PICKING UP PHYSIOLOGICAL MEASUREMENT SIGNALS, AND THEIR LEADS

BACKGROUND OF THE INVENTION

1. Field of the Invention

The present invention relates to a device for monitoring one or more measurement electrodes and a neutral electrode, attached to a patient for recording physiological measurement signals, and their leads while the measurement signals are being picked up, wherein each measurement electrode is connected to one input socket of an associated measurement amplifier.

2. Description of the Prior Art

In "ECG Electrodes: A Study of Electrical and Mechanical Long-Term Properties", Acta anaesth. Scand. 1979, 23, pp. 189–206, P. Ask et al. describe the measurement of electrode impedances in order to check the quality and adhesion to skin of ECG electrodes. Sinusoidal currents at different frequencies are applied to a pair of ECG electrodes, connected in series, and a reference resistance. Individual electrode impedances are determined from the amplitudes and phases of the ensuing applied voltage and the voltage measured across the resistance.

U.S. Pat. Nos. 4,658,831, 4,917,099 and 4,993,423 describe methods for detecting a detached electrode or interrupted lead line, wherein alternating current at one or more frequencies is applied to the measurement electrodes, and the ensuring voltages are measured. U.S. Pat. Nos. 4,919,145 and 5,020,541 further describe the monitoring of the impedance of ECG electrodes and their leads with the use of two phase-shifted carrier wave signals. These methods fail to supply any absolute value for the individual electrode impedances. Instead, a value is obtained which depends (sum or difference) on the impedances of a number of ECG electrodes, and the impedance of the neutral electrode is not measured. Moreover, is it not possible in these known systems to detect when a specific ECG electrode is in the process of becoming detached. The use of current at different frequencies further leads to an additional measurement difficulty, since electrode impedance varies with frequency.

The use of direct current for detection of electrode detachment or interruption in e.g. electrocardiography is also known. Contact impedance increases if a measurement electrode starts to detach from the patient. Here, an increase in DC potential across the electrode impedance can be achieved with an appropriately arranged resistor. When the potential exceeds a given value, the electrode is no longer viewed as being connected, i.e., a detached lead. The use of direct current for this detection has shortcomings, however, since electrode impedance is not purely resistive. There is some degree of polarization which differs for different types of electrodes. The potential caused by the polarization cannot be distinguished from the potential caused by the detection current through the electrode, so the impedance required to enable detection of any disconnected electrode varies greatly with different types of electrodes.

Another shortcoming is the circumstance that impedance varies whenever the patient moves, voltage across the electrode being modulated in step with the movements, thereby causing noise at about 1 Hz. These baseline variations are hard to filter out of the overall ECG without affecting the ECG signal itself. If possible, non-polarized electrodes, i.e. electrodes with very limited DC offset caused by polarization, are used to avoid baseline variations. The shortcoming here is the need to add a DC potential merely to detect whether or not the electrode is connected.

Reliable monitoring of measurement electrodes attached to the patient is important, so that a warning is issued before the electrode falls off. Electrode impedance increases when the electrode paste starts drying or the electrode begins to detach, thereby distorting the measurement by increasing noise. The measurement signal can also be damped when electrode impedances are very high, possibly causing a faulty diagnosis. Thus, there are e.g. instructions for ensuring a correct absolute value for e.g. ECG signal. Inaccuracies in electrodes leads can cause similar errors.

German OS 41 06 857 describes a device for processing physiological measurement signals, whereby a pulse is delivered to the patient's body via an additional electrode which, via the body's impedance, is electrically connected to measurement electrodes attached to the patient. The measurement electrodes' contact with the patient's body can be checked by studying the measurement electrodes' response to the pulse. This check on the measurement electrodes and their leads, however, is only performed when enabled by the operator, i.e. when she/he presses a button. For continuous monitoring of the electrodes, this function must be supplemented with another method, e.g. the aforementioned DC monitoring.

SUMMARY OF THE INVENTION

An object of the present invention is to provide a device which allows monitoring of measurement electrodes and a neutral electrode attached to a patient, plus associated leads, at the same time as physiological measurement signals are being recorded, thereby eliminating the aforementioned shortcomings of the prior art.

The above object is achieved in accordance with the principles of the present invention in a device for monitoring at least one of a plurality of measurement electrodes and a neutral electrode attached to a patient for recording physiological measurement signals, as well as the leads of these electrodes, while the measurement signals are being picked up from the patient, the device including a plurality of measurement amplifiers with each measurement electrode being connected to an input of an associated measurement amplifier, and a test signal generator which generates a pure AC signal as a test signal, without any direct current component, the test signal being applied to the neutral electrode during the pick up of the physiological measurement signals from the patient.

The device according to the invention thus utilizes the reference or neutral electrode attached to the patient for delivering a continuous, pure AC signal without any direct current component. This permits continuous monitoring of the measurement electrodes and their contact with the patient during recording, and the problems associated with DC charging of the electrodes are avoided. In addition to reducing baseline drift problems, reduced electrode charging makes possible the use of cheaper electrodes without a DC offset causing saturation of the amplifier, with the device according to the invention, measurement of electrode impedance is also performed without any reduction in input impedance to the following measurement amplifier. This is important, since reduced input impedance would degrade the ECG signal.

In an embodiment of the device according to the invention, a first measurement unit is connected to the measurement amplifier's output terminals to measure the output signals arising from the test signal and for detecting, from the output signals, any faulty electrode contact and/or leads, the first measurement unit being arranged to determine the difference, in an optional manner, between the output signals, triggered by the test signal, from any two of the measurement amplifiers. In normal, fault-free operation, the test signal causes signals of equal magnitude to appear on all amplifier input terminals, and these signals disappear when subtracted from each other in the derived signal formation. If an electrode is poorly attached, however, its electrode impedance will be high, and the signal generated by the test signal on the relevant measurement amplifier input terminal will, then be smaller because of voltage division between the electrode impedance and the amplifier input impedance, and a residual signal from the test signal will remain after difference determination according to the above, thereby indicating that an electrode is poorly attached.

In another embodiment of the invention, a switch is connected to the test signal generator's output terminal in order to switch the test signal, in an optional manner, between the neutral electrode and the input terminal of one of the measurement amplifiers. The device can therefore even be used for calibrating the measurement amplifiers. This calibration is performed at some suitable point in time, e.g. in conjunction with device start-up. For this purpose the test signal is switched to the selected measurement amplifier's input terminal without first passing through the patient. This is repeated for each channel with amplitude being measured in the different channels and gain being adjusted so all channels have the same amplitude. Absolute accuracy is limited only by the accuracy of the test signal, whereas relative accuracy can be greater. Measuring the entire frequency range and calibrating same are also possible. Calibrating the amplifiers is important for common mode suppression, and the relationship between them is important to the removal of noise, AC line hum in particular. Calibrating the amplifiers is also important to attaining a correct magnitude for the ECG signal, since the measured absolute value is of importance.

According to another embodiment of the device of the invention, the frequency of the test signal generator lies above the frequency range relevant to the ECG signal, preferably above 250 Hz. The device according to the invention operates to advantage digitally with a sampling rate of e.g. 1 kHz. A faster sampling rate is employed for the actual measurement, and down-sampling is performed after derived signal formation. This normally causes the test signal to disappear. It should also be noted that electrode impedance is frequency-related with a lower impedance at a higher frequency.

DESCRIPTION OF THE DRAWINGS

FIG. 5 is a schematic block diagram of a third embodiment of a device constructed in accordance with the principles of the present invention.

FIG. 6 is a schematic block diagram of a fourth embodiment of a device constructed in accordance with the principles of the present invention.

DESCRIPTION OF THE PREFERRED EMBODIMENTS

Figure 1:
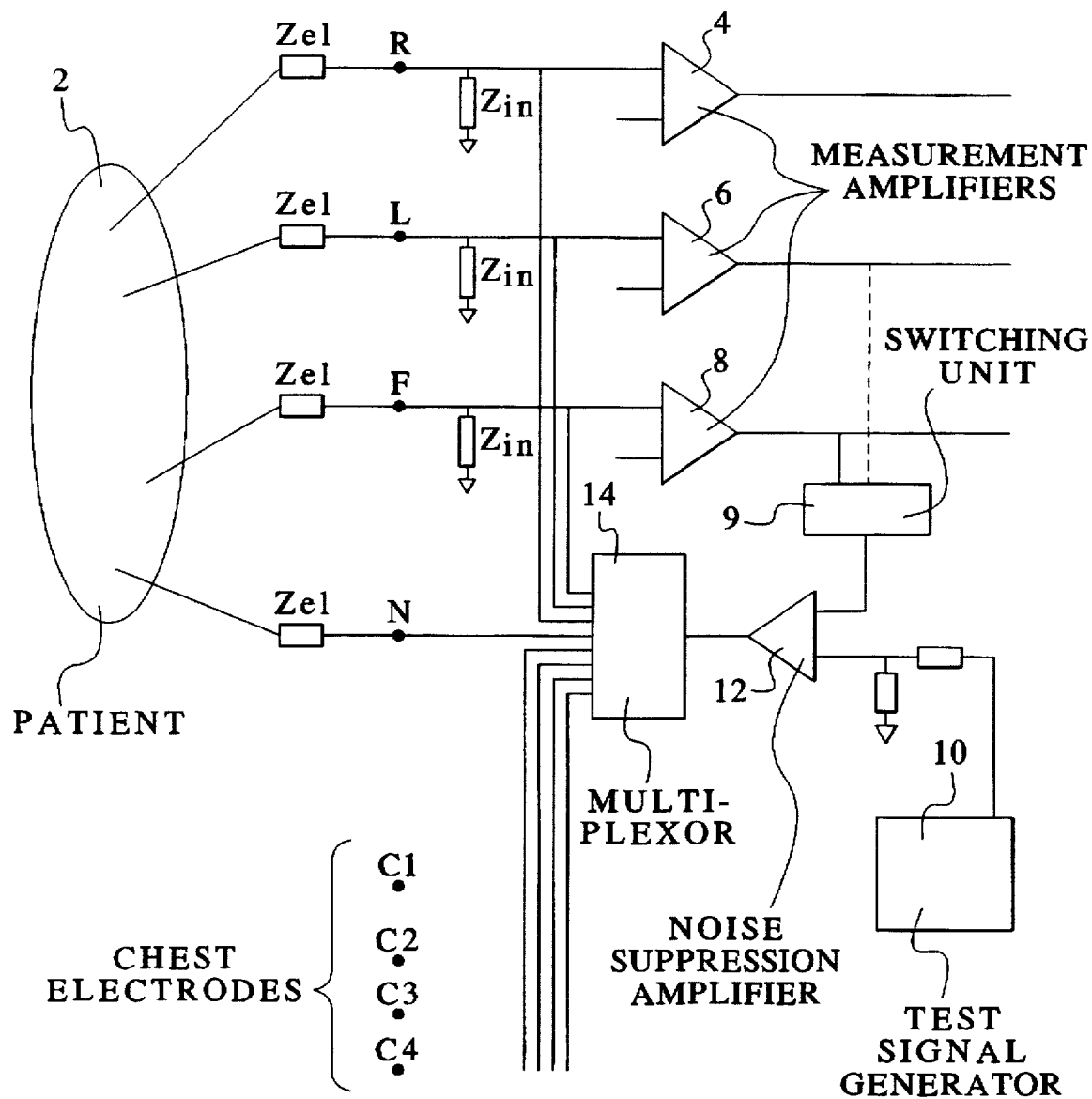
FIG. 1 is a schematic block diagram of a first embodiment of a device constructed in accordance with the principles of the present invention.

FIG. 1 shows a first embodiment of a device according to the invention for continuous monitoring of measurement electrodes, attached to a patient 2 for recording physiological measurement signals via multiple channels, i.e., R (right arm), L (left arm), F (foot) and their leads. Each measurement electrode R, L, F is connected to one of the input terminals on its associated measurement amplifier 4, 6 and 8. The other input terminals of the other measurement amplifiers 4, 6 and 8 are connected to a common reference potential. The physiological signals to be measured are, e.g., ECG signals.

A test signal generator 10 sends a test signal, in the form of a continuous, pure alternating current signal without any direct current component, to the neutral electrode N via a noise suppression amplifier 12 and switching means in the form of a multiplexor 14. The noise suppression amplifier 12 is connected, via a switching unit 9, to the output terminal or terminals of one or more of the measurement amplifiers 4, 6 and 8.

The contact impedances of the electrodes R, L, F, N and the impedance of associated leads are represented in FIG. 1 by the impedances $Z_{el}$, and input impedances are represented by $Z_{in}$.

In FIG. 1, C1, C2, C3 and C4 represent other ECG electrodes for application to, e.g., the chest.

Since all of the electrodes attached to the patient's body are electrically interconnected by the body's impedance, the signal applied via the neutral electrode N will give rise to a response signal in each of the measurement channels R, L and F, and these response signals are continuously measured at the same time as the ECG recording.

The task of the neutral electrode N is to ensure that the measurement amplifier's floating ground has the same potential as the patient 2. The patient's potential, which must be floating for safety reasons, is determined by stray capacitances to the surroundings, especially ground and nearby power cables. The entire floating amplifier system also has stray capacitances to ground and line voltage. The relationship between these capacitances is normally not the same for the patient and for the amplifiers, so a potential difference exists between the patient and amplifiers. The neutral electrode reduce this difference. A hum current will then pass through the neutral electrode, and a voltage drop will then develop because of the neutral electrode's impedance. If the neutral electrode is directly connected to floating ground, this voltage drop will be detected as a voltage between the patient and the amplifiers' ground. In an effort to reduce this voltage, the signal is fed from a measurement electrode, via the noise suppression amplifier 12, back to the patient via the neutral electrode N. The voltage gradient between the patient and amplifier ground will then drop by the gain in the feedback loop. The noise suppression amplifier 12, which is part of this feedback loop, is used in the device according to the invention as the test signal amplifier in order to apply the test signal, with which electrode impedances are measured, to the patient 2.

Since impedance in the body are normally on the order of 100 Ω, whereas electrode impedance is normally on The order of 10–100 kΩ, impedance in the body is therefore negligible compared to electrode impedance, and the test signal's response signals will accordingly be essentially the same on all amplifier input terminals. When derived signals are formed between two electrodes, the test signals response signal will therefore be eliminated by subtraction.

If, however, an electrode is e.g. poorly attached, the electrode impedance will be much higher, i.e. at MΩ levels, and there is a voltage division between the electrode impedance $Z_{el}$ and the amplifier's input impedance $Z_{in}$ in the channel in question. The test signals response signal (like the ECG signal) will then be smaller, a residue of the test signals response signal remaining after signal formation between two electrodes with differing impedances, e.g. because one electrode has become detached or is in the process of becoming detached. Faults in electrode leads produce similar results.

In certain instances, measuring the amplitude of the test signals response signal at the respective outputs of the measurement amplifiers 4, 6 and 8 before derived signal formation may be preferable.

When an imbalance develops in electrode impedances because of faulty electrode contact or faulty electrode leads, the test signals residual response signal can be allowed to remain if sufficiently small, or it can be eliminated by subtraction or filtering. Removal of the residual signal by subtraction can be performed with an appropriate subtraction signal generated by the test signal generator.

Output signals from the measurement amplifiers 4, 6 and 8 are appropriately sent to an A/D converter for subsequent digital signal processing (not described herein). The residual response signal persisting when there is imbalance in the electrode impedances $Z_{el}$ disappears if the frequency is appropriate. If the test signal has a frequency of e.g. 1 kHz, it will disappear in down-sampling to 1 k sps. The original sampling rate must have been faster for the test signal to be measured in digital form.

The ability to remove the test signals response signal from measurement signals is a requirement for performing continuous test measurements.

The test performed with the device according to the invention is a relatively rough test which supplies a warning when the contact paste or electrode glue has dried and the electrode has become detached, or is in the processing of becoming detached, before the electrode drops off or a when a fault has developed in leads. Erroneous diagnoses caused by a damping of the ECG signal by high impedance in the electrode used for measurement is thereby avoided with the device according to the invention. No direct current nor any special test pulse need to be used for detection of lead loss. This reduces charging of the electrodes with less baseline variation as a result. Reduced charging of the electrodes also makes possible the use of cheaper electrodes without amplifier saturation caused by DC offset. This means that narrower amplifier dynamics are needed than in the use of direct current. The impedance measurement required for electrode monitoring is performed with the device according to the invention without any drop in input impedance to the measurement amplifiers which would degrade the ECG signal.

The device according to the invention can also be used for calibrating the measurement amplifiers 4, 6 and 8, including the following A/D converter (not shown). For this purpose, the test signal is switched with the switching stage 14, in the form of a number of switches, straight to one of the input terminals of the amplifiers 4, 6 and 8 without passing the patient 2. The amplitude of the test signal is measured in the various measurement channels, and gain is calibrated so it is of equal magnitude in all channels. The absolute accuracy of calibration is governed by the accuracy of the test signal, but relative accuracy can be greater.

The device according to the invention can also be used to measure the entire frequency range and to calibrate same.

Correct calibration of the amplifiers 4, 6 and 8 is important to common mode suppression, and the relationship between the amplifiers 4, 6 and 8 is important in eliminating noise, the greatest noise generally being AC line hum.

Figure 2:
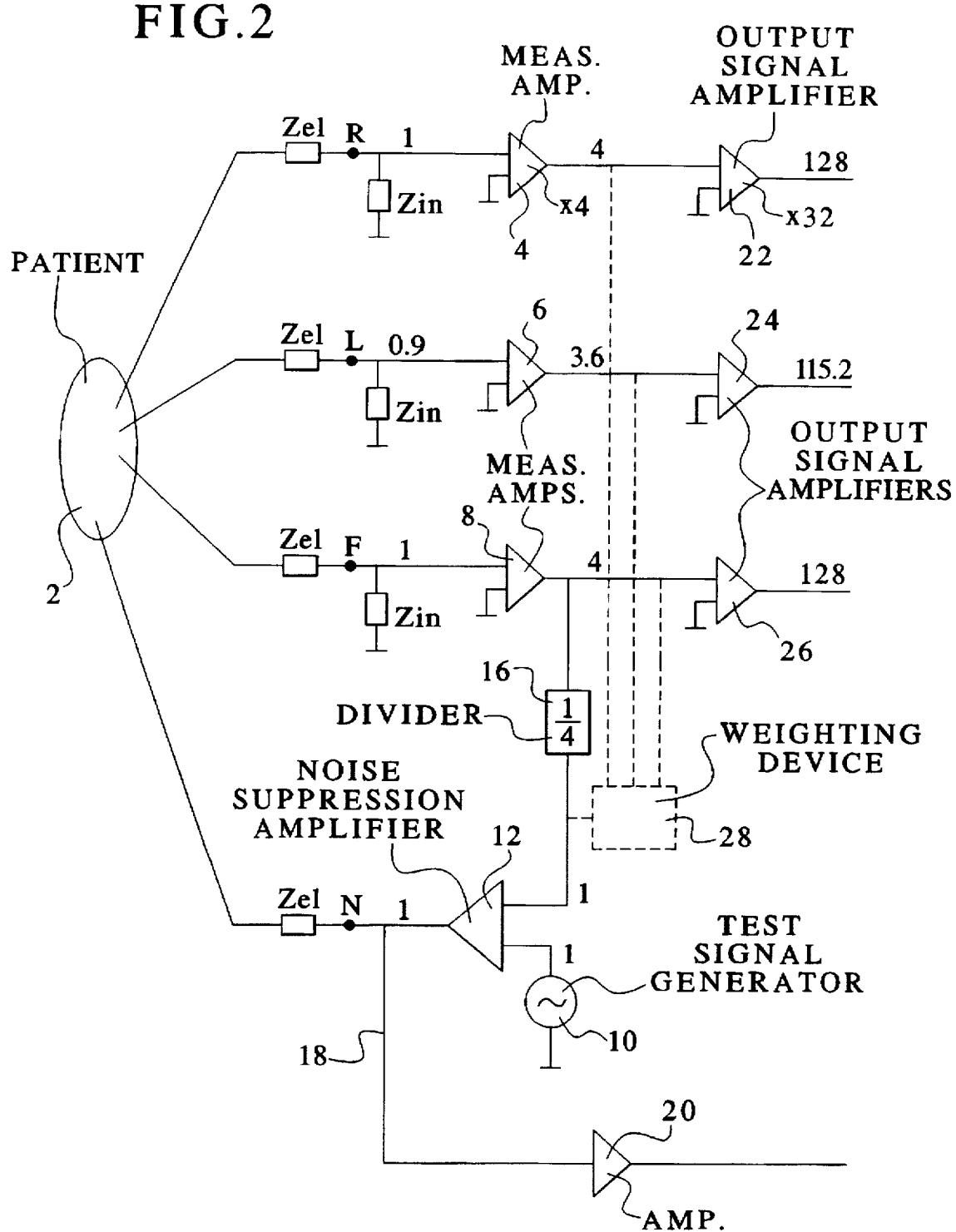
FIG. 2 is a schematic block diagram of a second embodiment of a device constructed in accordance with the principles of the present invention.

FIG. 2 shows a circuit diagram of an alternative embodiment of the device according to the invention, wherein the components and units corresponding to those in FIG. 1 are assigned the same designation as in FIG. 1. Moreover, the relative magnitude of the signals is shown at different points in the diagram, for certain examples of selected amplifier gains of the amplifiers.

In the embodiment according to FIG. 2, the test signal generator 10 is connected between the reference potential and one of the input terminals of the noise suppression amplifier 12, whereas the other input of the noise suppression amplifier 12 is connected to the output terminal of the measurement amplifier 8 in the F channel by a divider 16. There is also an output line 18 and a signal amplifier 20 for measuring the signal at the output terminal of the noise suppression amplifier 12. An alternative method for deriving the common mode signal to the input of the suppression amplifier 12 is indicated with the weighting device 28.

The noise suppression amplifier 12 receives a common mode signal, whereupon the signal from the test signal generator 10 passes straight through the amplifier 12, represented by the number "1" on the amplifier output terminal. In this instance, the electrodes for the R and F channels are assumed to be correctly attached, so the test signal is found virtually unchanged on the input terminals of the measurement amplifiers 4 and 8, represented at those locations by the number "1". In this embodiment, the amplifiers 4, 6 and 8 have a gain equal to 4, so the magnitude of the test signal at the output terminal of the measurement amplifier 8 is "4". This signal is sent back to the noise suppression amplifier 12, via the divider 16, which divides the signal to the same extent as it is amplified in the measurement amplifier 8 so the test signal recovers its original magnitude, and the noise suppression amplifier 12 thereafter operates in the common mode. Thus, the suppression 12 amplifier does not affect the test signal.

The output terminal on the measurement amplifier 4 accordingly receives a signal whose magnitude is "4".

In the illustrated example, it is further assumed that the contact for the L channel has detached or is in the process of becoming detached, so the electrode impedance $Z_{el}$ increases for this channel. As a result, the test signal will be damped in the L channel. In this example, the signal has been damped so its amplitude at the input terminal on the measurement amplifier 6 amounts to "0.9". The output signal from the measurement amplifier 6 accordingly amounts to "3.6".

Each of the measurement amplifiers 4, 6 and 8 is accompanied by an additional amplifier 22, 24 and 26 to produce the gain 32. Signals with the relative magnitudes "128", "115.2" and "128" are accordingly supplied at the output terminals of these amplifiers 22, 24 and 26. The magnitude of these signals designate a fault in the L channel. Determining whether the fault is caused by poor contact for the L electrode or the N (neutral) electrode, however, is not possible, since both these electrodes are part of the loop traversed by the signal in question.

Figure 3:
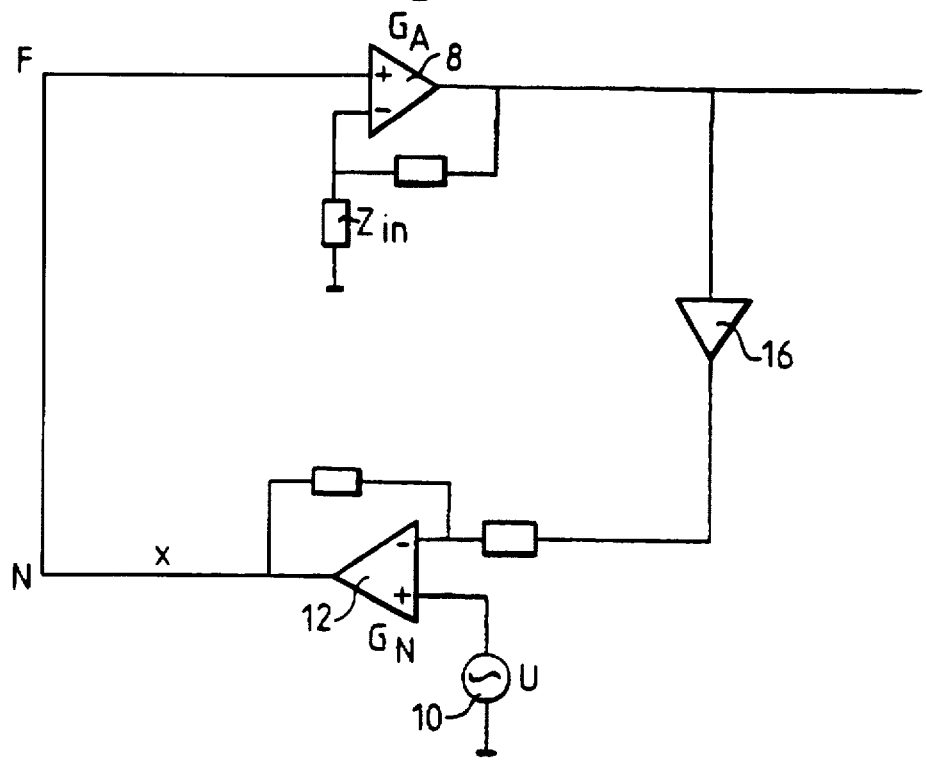
FIG. 3 illustrates the calculation of the transfer function in a circuit loop in the embodiment shown in FIG. 2.

FIG. 3 illustrates the loop, formed by the F channel and the N channel, for calculation of the transfer function for the test signal in the embodiment in FIG. 2.

The test signal from the test signal generator 10 is designated U, the noise suppression amplifier 12 has the gain $G_N$ and the signal on the noise suppression amplifier's 12 output terminal is designated x. The gain of the measurement amplifier 8 is designated $G_A$. FIG. 3 also contains some resistors which were not shown in FIG. 2 for simplicity.

With the aforementioned designations, the following applies:

$$x = U - G_N ((x \cdot G_A) - U)$$

The following is obtained from this relationship:

$$x = U \cdot \frac{1 + G_N}{1 + G_N \cdot G_A}$$

This means that x=U if the gain $G_A$ of the measurement amplifier 8 equals 1.

Thus, the divider 16, which divides the signal to the same extent as the measurement amplifier 8 amplifies it, serves as a attenuater in order to render gain equal to −1. In normal, fault-free cases, there is accordingly no impact on the test signal when it passes the noise suppression amplifier 12.

Figure 4:
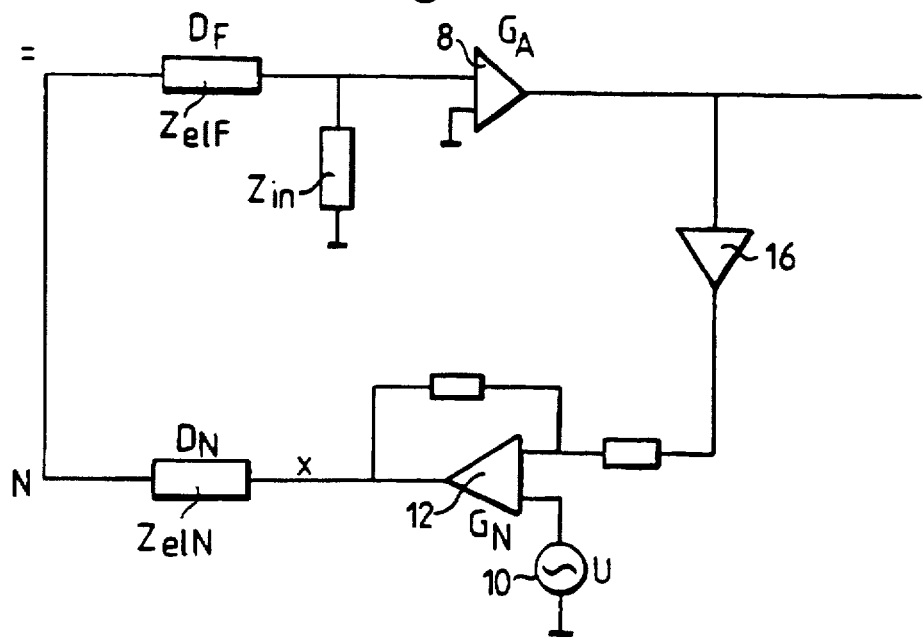
FIG. 4 shows the loop in FIG. 3 with input impedances.

FIG. 4 shows the same loop with the electrode impedances $Z_{el}$ and $Z_{elN}$ which cause the dampings $D_F$ and $D_N$ respectively.

If these dampings $D_F$ and $D_N$ are entered into the above equation, the following is obtained:

$$x = U \cdot \frac{1 + G_N}{1 + G_N \cdot G_A \cdot D_F \cdot D_N}$$

Thus, increased damping causes a reduction in the x/U ratio.

FIG. 5 shows another embodiment, which is suitable if the ECG amplifier system utilizes a coupling with a floating reference for the measurement amplifiers 4, 6 and 8. This reference is derived from one or more measurement electrodes. In this instance, the test signal is added to the reference in the same way as the test pulse in a device according to the previously discussed German OS 41 06 857. In this instance, the signal generator 10 can also be used to generate a test pulse, according to this published application. In the embodiment of FIG. 5, the test signal generator 10 is not referenced to the same potential as the input impedance $Z_{in}$ of the measurement amplifiers 4, 6 and 8, i.e., floating ground. The test signal or noise suppression amplifier 12, however, is referenced to floating ground and this accordingly ensures that most of the generated signal appear across the electrode impedance in series with the input impedance.

The corresponding components and units in FIGS. 1 and 2 were assigned the same designations in FIG. 5.

FIG. 6 show another embodiment of the device according to the invention in which the test signal generator 10 is grounded, but the measurement amplifiers 4, 6, 8 are floating. The same designations were also used here for the same components and units as in previously described embodiments.

In this instance, it is assumed that there is an electrode fault in the L channel in the same way as in the embodiment according to FIG. 2. In the embodiment according to FIG. 6, the test signal normally has the same magnitude at both input channels on all the measurement amplifiers 4, 6 and 8. The entire signal is then common mode, so it is not amplified, i.e. the amplifiers, common mode gain is equal to 1. As a result of the fault in the L channel, a difference arises between the input of the measurement amplifier 6. This difference amounts to "0.1", the "normal" signal strength amounting to "1" in the same way as in FIG. 2. This "0.1" difference is amplified in the measurement amplifier 6 whose gain is assumed to be equal to "4", as was the case in FIG. 2. The output signal from the amplifier 6 therefore amounts to 1−0.4="0.6".

Following amplifiers 22 and 26 in the fault-free channels R and F also receive a common mode signal, which is not amplified, whereas the ensuing difference between the input of the amplifier 24 (equal to 0.4) is amplified in this amplifier to "−12.8" by the assumed gain 32. The output signal from the amplifier 24 is negative because the signal at the amplifier's positive input terminal is smaller than the normal signal fed to the negative input channel.

As is apparent, the magnitudes of the output signals are small compared to the signals in the embodiment according to FIG. 2, at the same time as the fault in the L channel produces a highly deviant signal. Since the output signals are relatively small, a large amplitude can be used for the test signal, making possible measurement of comparatively small impedances. Relatively sensitive fault detection is therefore achieved.

Figure 7:
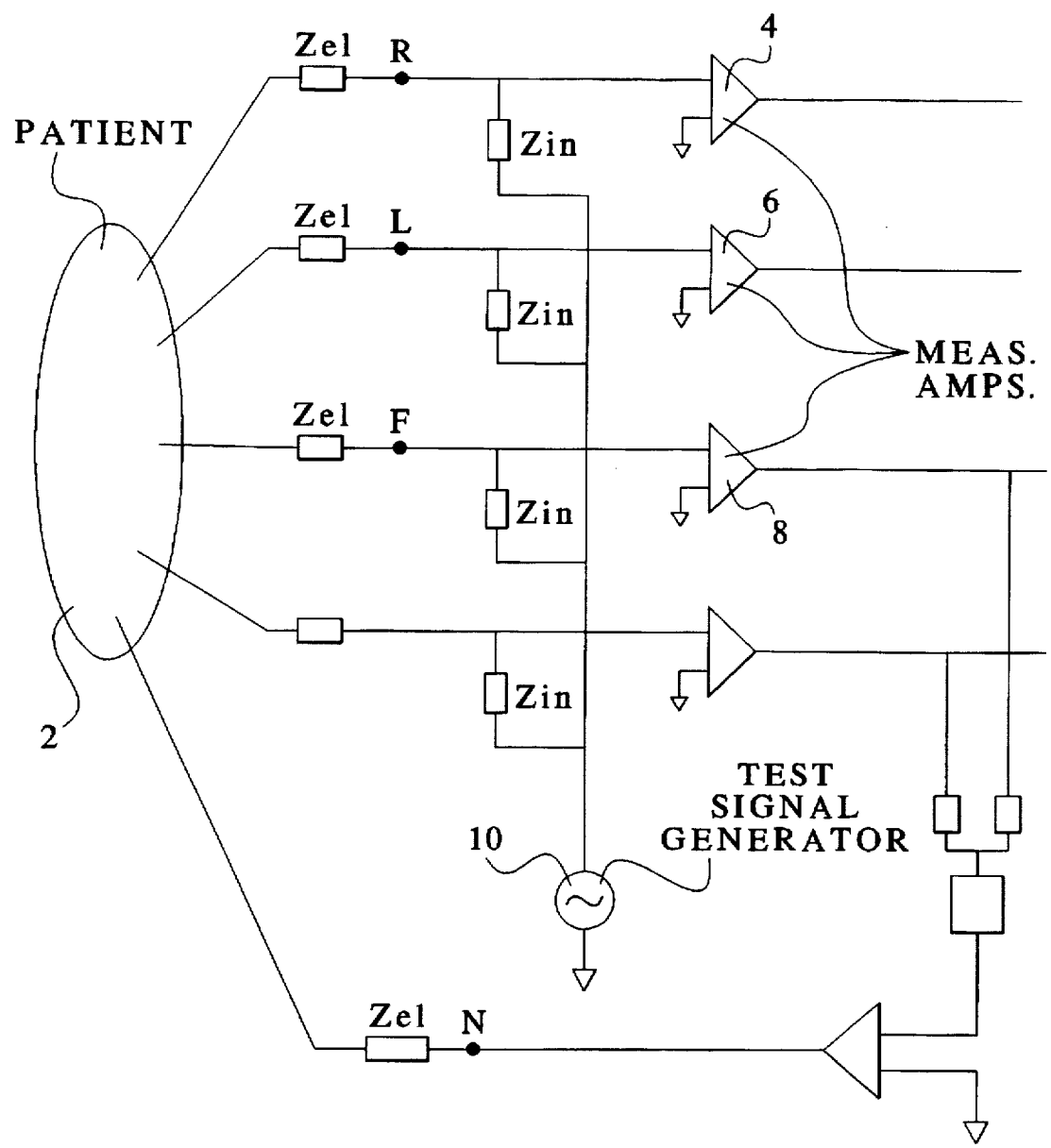
FIG. 7 is a schematic block diagram of a fifth embodiment of a device constructed in accordance with the principles of the present invention.

As noted above, it is essential for the test signal, applied to the patient, to be referenced to the same potential as the measurement amplifiers' input impedances $Z_{in}$ for the applied test signal to be damped by the input impedance $Z_{in}$. This means that the test signal generator must generate a test signal across the electrode impedance $Z_{el}$ and the input impedance $Z_{in}$. This can be done in a more direct way. One such embodiment is shown in FIG. 7.

Here, the test signal is added to the respective inputs of the measurement amplifiers 4, 6 and 8. Injection of the test signal can be performed via the existing input impedance $Z_{in}$ or, alternatively, added with an additional component, e.g. a resistor or capacitor.

With low-resistance electrodes, the added test signal is very small in this case, and the result is essentially the same as in the embodiment shown in FIG. 6, i.e. a relatively large signal amplitude can be used, thereby facilitating measurement of small impedances.

Figure 8:
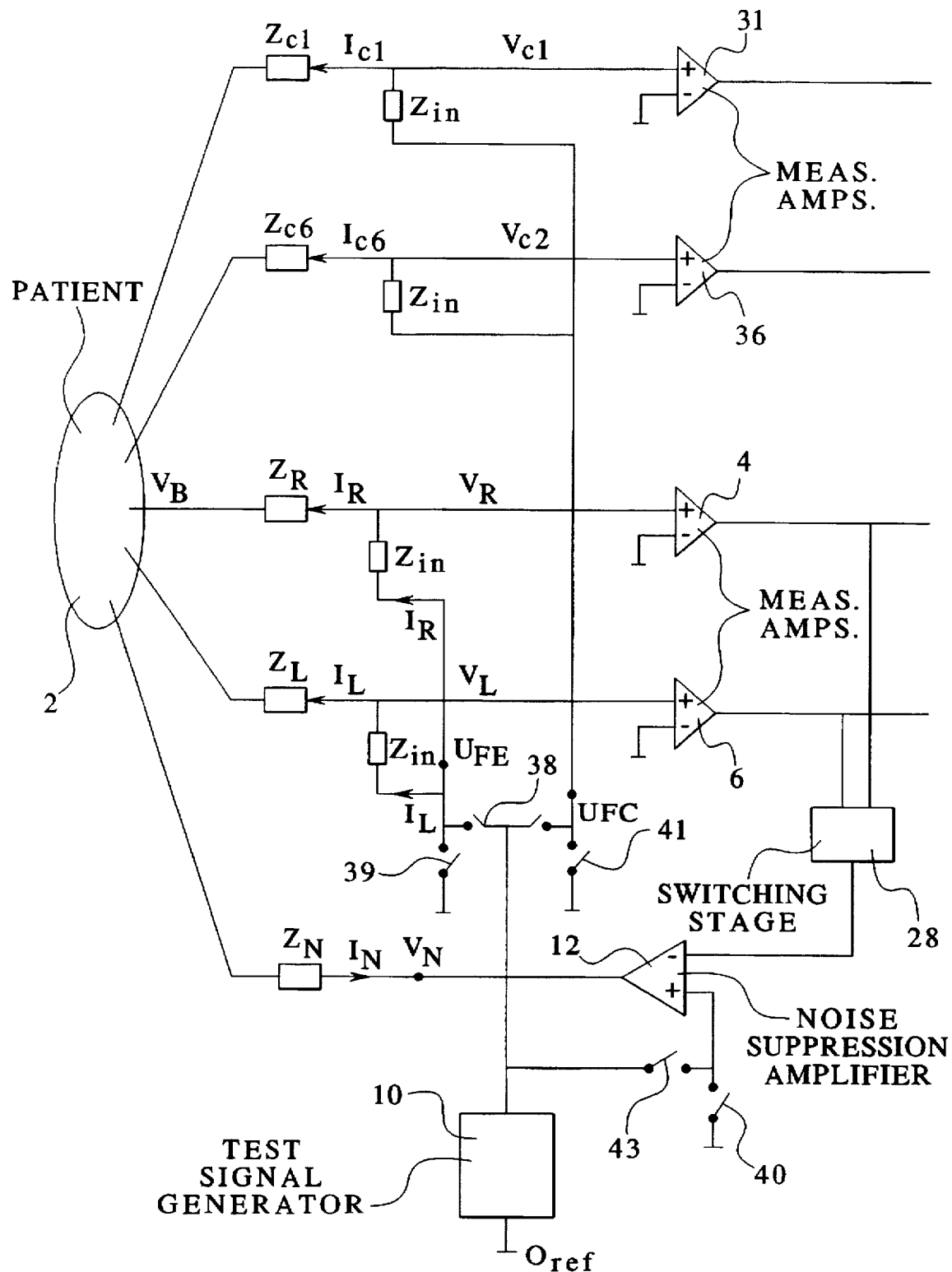
FIG. 8 is a schematic block diagram of a sixth embodiment of a device constructed in accordance with the principles of the present invention.

FIG. 8 shows an embodiment of the device according to the invention, making it possible to locate the fault with even greater accuracy and even to measure the impedance of individual electrodes. Here, the measurement signal can be applied in two different ways, and measurement is performed twice. The two measurements can either be made at two different times or simultaneously at two different frequencies. The measurement amplifiers are divided into two groups. The first group of measurement amplifiers 4 and 6 are connected to the extremity electrodes R and L, and associated measurement signals are fed back to the noise suppression amplifier 12 as described above.

The second group of measurement amplifiers 31 . . . 36, connected to the chest electrodes C1 . . . C6, do not feed back the signal. All amplifier input terminals have an input impedance $Z_{in}$ coupled to a for the group common potential, i.e. designated $U_{FE}$ for the first group and $U_{FC}$ for the second group.

In the first measurement, the output of the test signal generator 10 is switched with the switch 38 to point $U_{FC}$.

whereas point $U_{FE}$ and the noise suppression amplifier 12 positive input terminal are switched with the switches 39 and 40 to the zero reference $0_{ref}$ of the test generator 10. Measurement currents to the patient 2 via the measurement electrodes are obtained from the equations (1) and (2) below $$I_{cx} = \frac{U_{FC} - V_{cx}}{Z_{in}} \quad (1)$$

$$I_R = \frac{U_{FE} - V_R}{Z_{in}} \quad (2)$$

in which $I_{CX}$ and $I_R$ designate current to the measurement electrode cx with the electrode impedance $Z_{CX}$ in FIG. 8 and current to the measurement electrode R with the electrode impedance $Z_R$. $V_{CX}$ and $V_R$ designate the potential of the corresponding leads and $Z_{in}$ designates the input impedance of the associated measurement amplifier.

For $U_{FE}$=0, $U_{FC}$ set at 1 and $Z_{in}$ set at 10 Mohms (10M), the following is obtained:

$$I_{cx} = \frac{1 - V_{cx}}{10M} \text{ and } I_R = \frac{-V_R}{10M} \text{ respectively.}$$

The sum of these currents $I_N$ $$I_N = \Sigma I_{CX} + I_R + I_L + I_F \quad (3)$$

is found on the neutral electrode N.

If an approximation is made in which the patient's potential $V_{body}$ is not affected by the electrode impedances in the first group, the patient's potential $V_{body}$ can be obtained from the equation (4) below:

$$V_{body} = \frac{V_N}{G_N} \quad (4)$$

in which $V_N$ designates the potential of the lead to the neutral electrode N.

For $G_N$=−10, the following is obtained $$V_{body} = -\frac{V_N}{10}$$

From this value for $V_{body}$, the impedances $Z_{CX}$ of the chest electrodes C1 . . . C6 are obtained from the equation (5) below and the neutral electrode's N impedance $Z_N$ from the equation (6).

$$z_{cx} = \frac{V_{cx} - V_{body}}{I_{cx}} = \frac{V_{cx} + \frac{V_N}{10}}{I_{cx}} \quad (5)$$

$$Z_N = \frac{V_{body} - V_N}{I_N} = -\frac{1.1 V_N}{I_N} \quad (6)$$

In measurement number 2, the point $U_{FC}$ is connected with the switctes 38 and 41 to the zero reference $0_{ref}$. The positive input of the noise suppression amplifier 12 remains connected to the zero reference $0_{ref}$ of the test signal generator 10 via the switch 40.

In this instance, the measurement currents are supplied by the equations (7) and (8) below.

$$I_{cx} = \frac{U_{FC} - V_{cx}}{Z_{in}} \quad (7)$$

$$I_R = \frac{U_{FE} - V_R}{Z_{in}} \quad (8)$$

For $U_{FC}$=0 and $U_{FE}$ and $Z_{in}$ set at 1 and 10 Mohms respectively, the following is obtained:

$$I_{cx} = -\frac{V_{cx}}{10M} \text{ and } I_R = \frac{1 - V_R}{10M} \text{ respectively}$$

Even in this instance, the current $I_N$ across the neutral electrode N is equal to the sum of the other electrodes, currents according to the equation (9) below.

$$I_N = \Sigma I_{CX} + I_R + I_L + I_F \quad (9)$$

The potential $V_{body}$ of the patient 2 can now be calculated with the aid of the current $I_N$, and the potential $V_N$ mesured at the output of the noise suppresion amplifier 10, and with the value of the impedance $Z_N$ of the neutral electrode N that was calculated in the measurement number one (se equation (6)):

$$V_{body} = V_N + (I_N \cdot Z_N) \quad (10)$$

Finally, the impedance $Z_R$ of the extremity limb R can be calculated with the equation (11) below:

$$Z_R = \frac{V_R - V_{body}}{I_R} \quad (11)$$

The impedances $Z_L$ etc. in the other limb electrodes L etc. are calculated in an analogous manner.

The accuracy of calculations of electrode impedances is primarily dependent by the approximation made in the first measurement.

The switch 43 in FIG. 8 must be closed when the amplifiers are calibrated, as described in connection with FIG. 1 above.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for obtaining and measuring physiological measurement signals comprising:

a plurality of measurement electrodes and a neutral electrode adapted for attachment to a patient for picking up physiological measurement signals from said patient, each electrode being connected to an electrode lead, and means for monitoring said electrodes and said leads for faults during pick-up of said measurement signals comprising a plurality of measurement amplifiers respectively connected to said leads and each amplifier having an output, said amplifiers being arranged in two groups, each group containing at least one of said amplifiers, a noise suppression amplifier having a first input connected only to the outputs of a first of said two groups of amplifiers, and test signal generator means for generating a first alternating current signal through an input impedance and an associated electrode impedance of each of the amplifiers in a second of said two groups of measurement amplifiers, and for generating a second alternating current through the input impedance and associated electrode impedance of each of said amplifiers in said first group, and means for measuring voltages generated by said two alternating current signals.

2. The device according to claim 1 wherein said test signal generator comprises means for generating a test signal as a voltage between two poles and wherein said noise suppression amplifier has a second input, in a first phase, connecting said first pole of said test signal generator to said second input of said noise suppression amplifier and, via separate impedances, to input terminals of measurement amplifiers in the first group and connecting said second pole of said test signal generator, via separate impedances, to input terminals of measurement amplifiers in the second group and, in a second phase, connecting said first pole of said test signal generator to said second input of said noise suppression amplifier and, via separate impedances, to input terminals of measurement amplifiers in the second group and connecting said second pole of said test signal generator, via separate impedances, to input terminals of measurement amplifiers in the first group.

3. The device according to claim 1 wherein said test signal generator means comprises a first test signal generator which generates said first alternating current signal at a first frequency and a second test signal generator which generates said second alternating current signal at a second frequency, each of said first and second test signal generators respectively having first and second poles, and said device further comprising means for connecting said first pole of said first signal generator to a second input of said noise suppression amplifier and, via separate impedances, to inputs of said measurement amplifiers in the first group and for connecting said second pole of said first test signal generator, via individual impedances, to the inputs of the measurement amplifiers in the second group, while connecting said first pole of said second test signal generator to said second input of said noise suppression amplifier and, via individual impedances, to the inputs of measurement amplifiers in the second group and for connecting said second pole of said second test signal generator, via individual impedances, to the inputs of the measurement amplifiers in said first group.

4. The device according to claim 1, further comprising measurement means connected for measuring a potential at an output of the noise suppression amplifier.

5. The device according to claim 1, further comprising measurement means connected to respective outputs of the measurement amplifier, for measuring output signals of said measurement amplifier resulting from the test signals and for detecting from said output signals faults in electrode contact and leads.

6. The device according to claim 1, wherein said first measurement means comprises means for forming a difference between the output signals, resulting from the test signal, from any selected two of the measurement amplifiers.

7. The device according to claim 1, wherein the physiological measurement signals are ECG signals, and further comprising measurement means employing a fast sampling rate for measuring the physiological measurement signals, and for performing downsampling, after derived signal formation, to eliminate the test signal.

8. The device according to claim 1, wherein the test signal is a sinusoidal signal, and further comprising a plurality of narrow band block filters respectively connected to outputs of the measurement amplifiers to remove the test signal from measurement signals.

9. The device according to claim 1, further comprising switching means are connected to an output of the test signal generator for selectively switching the test signal between said neutral electrode and an input of one of the measurement amplifiers.

10. The device according to claim 1, wherein said test signal generator means comprises means for generating a test signal having an amplitude which is negligible compared to respective amplitudes of the measurement signals.

11. The device according to claim 1, wherein said test signal generator means comprises means for generating a test signal having a frequency outside a frequency range for ECG signals.

12. The device according to claim 11 wherein said test signal generator means comprises means for generating a test signal having a frequency below 1 Hz.

13. The device according to claim 11 wherein said test signal generator means comprises means for generating a test signal having a frequency greater than 250 Hz.

* * * * *